(12) United States Patent
Barrett et al.

(10) Patent No.: US 6,506,798 B1
(45) Date of Patent: Jan. 14, 2003

(54) 4-ARYLAMINO, 4-ARYLOXY, AND 4-ARYLTHIO DIARYLAMINES AND DERIVATIVES THEREOF AS SELECTIVE MEK INHIBITORS

(75) Inventors: Stephen Barrett, Hartland, MI (US); Haile Tecle, Ann Arbor, MI (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 09/889,084
(22) PCT Filed: Dec. 21, 1999
(86) PCT No.: PCT/US99/30418
§ 371 (c)(1),
(2), (4) Date: Jul. 11, 2001
(87) PCT Pub. No.: WO00/41994
PCT Pub. Date: Jul. 20, 2000

Related U.S. Application Data

(63) Continuation-in-part of application No. 09/462,319, filed as application No. PCT/US98/13105 on Jun. 24, 1998, now Pat. No. 6,310,060.
(60) Provisional application No. 60/051,433, filed on Jul. 1, 1997.

(51) Int. Cl.[7] ............ A61K 31/195; A61K 31/24; C07C 229/00; C07C 205/00
(52) U.S. Cl. ............. 514/567; 514/535; 514/603; 514/618; 514/619; 514/621; 560/48; 562/435
(58) Field of Search ................. 514/539, 564, 514/603, 618, 619, 621, 535, 567; 562/430, 432, 434, 453, 435; 560/11, 13, 18, 21, 48; 564/162, 163

(56) References Cited

U.S. PATENT DOCUMENTS 5,068,250 A  11/1991  Penning et al.
5,525,625 A  6/1996  Bridges
6,310,060 B1 * 10/2001  Barret et al.

FOREIGN PATENT DOCUMENTS

| WO | WO93/24442 A1 | 12/1993 |
| WO | WO95/22992 A2 | 8/1995 |
| WO | WO97/07790 A1 | 3/1997 |
| WO | WO98/37881 A1 | 9/1998 |
| WO | WO99/01421 A1 | 1/1999 |
| WO | WO99/01426 A1 | 1/1999 |

OTHER PUBLICATIONS

PCT International Search Report PCT/US99/30418.

* cited by examiner

Primary Examiner—Johann Richter
Assistant Examiner—Paul A. Zucker
(74) Attorney, Agent, or Firm—Evelyn D. Shen; Suzanne M. Harvey

(57) ABSTRACT

The invention provides compounds of formula (II), wherein Ar, $R_3$, $R_4$, $R_5$, $R_6$, $R_7$, $R_8$ and W have the meanings given in the description. They are selective MEK inhibitors.

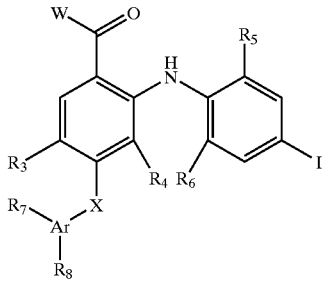

(II)

46 Claims, No Drawings

4-ARYLAMINO, 4-ARYLOXY, AND 4-ARYLTHIO DIARYLAMINES AND DERIVATIVES THEREOF AS SELECTIVE MEK INHIBITORS

This application is a continuation-in-part application of U.S. Ser. No. 09/462,319 filed Jan. 5, 2000, now U.S. Pat. No. 6,310,060 B1; which was a 35 U.S.C. 371 application from PCT/US98/13105 filed Jun. 24, 1998, which claims the benefit of priority to United States provisional application Serial No. 60/051,433 filed Jul. 1, 1997.

BACKGROUND

MEK enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated. Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinases. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

SUMMARY

The invention features compounds of formulae (II) below, such as formula(I):

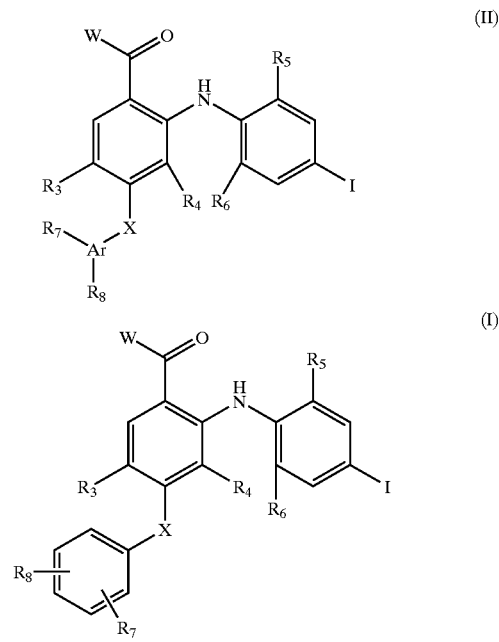

In formulae (I) and (II), W is $OR_1$, $NR_2OR_1$, $NR_AR_B$, $NR_2NR_AR_B$, or $NR_2(CH_2)_{2-4}NR_AR_B$. $R_1$ is H, $C_{1-8}$ alkyl, $C_{3-8}$ alkenyl, $C_{3-8}$ alkynyl, $C_{3-8}$ cycloalkyl, phenyl, (phenyl)$C_{1-4}$ alkyl, (phenyl)$C_{3-4}$ alkenyl, (phenyl)$C_{3-4}$ alkynyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, ($C_{3-8}$ heterocyclic radical)$C_{3-4}$ alkenyl, ($C_{3-8}$ heterocyclic radical)$C_{3-4}$ alkynyl, or $(CH_2)_{2-4}NR_AR_B$. $R_2$ is H, phenyl, $C_{1-4}$ alkyl, $C_{3-4}$ alkenyl $C_{3-8}$ alkynyl, $C_{3-8}$ cycloalkyl, or ($C_{3-8}$ cycloalkyl)$C_{1-4}$ alkyl. $R_A$ is H, $C_{1-6}$ alkyl, $C_{3-8}$ alkenyl, $C_{3-8}$ alkynyl, $C_{3-8}$ cycloalkyl, phenyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, (aminosulfonyl)phenyl, [(aminosulfonyl)phenyl]$C_{1-4}$ alkyl, (aminosulfonyl)$C_{1-6}$ alkyl, (aminosulfonyl)$C_{3-6}$ cycloalkyl, or [(aminosulfonyl)$C_{3-6}$ cycloalkyl]$C_{1-4}$ alkyl. $R_B$ is H, $C_{1-8}$ alkyl, $C_{3-8}$ alkenyl, $C_{3-8}$ alkynyl, $C_{3-8}$ cycloalkyl, or $C_{6-8}$ aryl. $R_3$ is halo, $NO_2$, $SO_2NR_J(CH_2)_{2-4}NR_ER_F$, $SO_2NR_JR_K$ or (CO)T. T is $C_{1-8}$ alkyl, $C_{3-8}$ cycloalkyl, $(NR_ER_F)C_{1-4}$ alkyl, $OR_F$, $NR_J(CH_2)_{2-4}NR_ER_F$, or $NR_ER_F$. $R_4$ is H or F; $R_5$ is H, methyl, halo, or $NO_2$; and $R_6$ is H, methyl, halo, or $NO_2$. In formula (II), Ar is phenyl, 2-pyridyl, 3-pyridyl, or 4-pyridyl. Each of $R_7$ and $R_8$ is independently selected from H, halo, $C_{1-4}$ alkyl, $SO_2NR_J(CH_2)_{2-4}NR_GR_H$, $(CO)(CH_2)_{2-4}NR_GR_H$, $(CO)NR_J(CH_2)_{2-4}NR_GR_H$, $(CO)O(CH_2)_{2-4}NR_GR_H$, $SO_2NR_GR_H$, and $(CO)NR_GR_H$. However, where Ar is a pyridyl, each of $R_7$ and $R_8$ is H. Each of $R_C$, $R_D$, $R_E$, $R_F$, $R_G$, and $R_H$ is independently selected from H, $C_{1-4}$ alkyl, $C_{3-4}$ alkenyl, $C_{3-4}$ alkynyl, $C_{3-6}$ cycloalkyl, and phenyl. Each of $NR_CR_D$, $NR_ER_F$, and $NR_GR_H$ can also be independently morpholinyl, piperazinyl, pyrrolidinyl, or piperadinyl. Each of $R_I$ and $R_J$ is independently H. methyl, or ethyl. $R_K$ is $C_{1-4}$ alkyl, $C_{3-4}$ alkenyl, $C_{3-4}$ alkynyl, $C_{3-6}$ cycloalkyl, or phenyl. X is O, S, or NH. Finally, each hydrocarbon radical or heterocyclic radical above is optionally substituted with between 1 and 3 substituents independently selected from halo, $C_{1-4}$ alkyl, $C_{3-6}$ cycloalkyl, $C_{1-4}$ alkenyl, $C_{1-4}$ alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$ alkyl, hydroxyl, amino, and $NO_2$. In addition to the above compounds, the invention also provides a pharmaceutically acceptable salt or $C_{1-7}$ ester thereof.

The invention also relates to a pharmaceutical composition including (a) a diarylamine (e.g., of formula I) and (b) a pharmaceutically acceptable carrier.

The invention further relates to a method for treating proliferative diseases, such as cancer, restenosis, psoriasis, autoimmune disease, and atherosclerosis. Other aspects of the invention include methods for treating MEK-related cancer, tumors of the breast, lung, colorectal, pancreas, prostate, brain, kidney, or ovary, and other solid or hematopoietic cancers. Further aspects of the invention include methods for treating or reducing the symptoms of xenograft (organ, cell(s), limb, skin, or bone marrow transplant) rejection, osteoarthritis, rheumatoid arthritis, cystic fibrosis, hepatomegaly, cardiomegaly, complications of diabetes (including diabetic nephropathy and diabetic retinopathy), stroke, heart failure, septic shock, asthma, and Alzheimer's disease. Compounds of the invention are also useful as antiviral agents for treating viral infections such as HIV, hepatitis (B) virus (HBV), human papilloma virus (HPV), cytomegalovirus (CMV), and Epstein-Barr virus (EBV). The methods include administering to a patient in need of such treatment, or suffering from such a disease or condition, a pharmaceutically effective amount of a disclosed compound or pharmaceutical composition thereof.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H, 3H)-pyrimidinedione (5FU), flutamide, and gemcitabine.

The chemotherapy or radiation therapy may be administered before, concurrently, or after the administration of a disclosed compound according to the needs of the patient.

The invention also features synthetic intermediates and methods disclosed herein.

Other aspects of the invention are provided in the description, the examples, and the claims below.

DETAILED DESCRIPTION

The invention features diarylamine compounds of formula (I), pharmaceutical compositions thereof, and methods of using such compounds and compositions.

According to one aspect of the invention, the compounds are MEK inhibitors. MEK inhibition assays include the cascade assay for inhibitors of MAP kinase pathway described at column 6, line 36 to column 7, line 4 of U.S. Pat. No. 5,525,625 and the in vitro MEK assay at column 7, lines 4–27 of the same patent, the entire disclosure of which is incorporated by reference (see also Examples 2–5 below).

A. Terms

Certain terms are defined below and by their usage throughout this disclosure.

Alkyl groups include aliphatic (i.e., the subset of hydrocarbyl or hydrocarbon radical structures containing hydrogen and carbon atoms, but not containing heteroatoms in the skeleton, or unsaturated carbon-carbon bonds) with a free valence. Alkyl groups are understood to include straight chain and branched structures. Examples include methyl, ethyl, propyl, isopropyl, butyl, n-butyl, isobutyl, t-butyl, pentyl, isopentyl, 2,3-dimethylpropyl, hexyl, 2,3-dimethyl hexyl, 1,1-dimethylpentyl, heptyl, and octyl. Cycloalkyl groups include cyclopropyl, cyclobutyl, cyclopentyl, cyclohexyl, and cyclooctyl.

Alkyl groups can be substituted with 1, 2, 3 or more substituents which are independently selected from halo (fluoro, chloro, bromo, or iodo), hydroxy, amino, alkoxy, alkylamino, dialkylamino, cycloalkyl, aryl, aryloxy, arylalkyloxy, heterocyclic radical, and (heterocyclic radical) oxy. Specific examples include fluoromethyl, hydroxyethyl, 2,3-dihydroxyethyl, (2- or 3-furanyl)methyl, cyclopropylmethyl, benzyloxyethyl, (3-pyridinyl)methyl, (2- or 3-furanyl)methyl, (2-thienyl)ethyl, hydroxypropyl, aminocyclohexyl, 2-dimethylaminobutyl, methoxymethyl, N-pyridinylethyl, diethylaminoethyl, and cyclobutylmethyl.

Alkenyl groups are analogous to alkyl groups, but have at least one double bond (two adjacent $Sp^2$ carbon atoms). Depending on the placement of a double bond and substituents, if any, the geometry of the double bond may be entgegen (E), zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof; like alkyl groups, they may be straight chain or branched, and they may be substituted as described above and as exemplified throughout the disclosure. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl, and 2-methyl-2-propenyl. In formulae (I) and (II) alkenyls can be $C_{2-4}$ or $C_{2-8}$, and are preferably $C_{3-4}$ or $C_{3-8}$.

More general forms of substituted hydrocarbon radicals include hydroxyalkyl, hydroxyalkenyl, hydroxyalkynyl, hydroxycycloalkyl, hydroxyaryl, and corresponding forms for the prefixes amino-, halo- (e.g., fluoro-, chloro-, or bromo-), nitro-, alkyl-, phenyl-, cycloalkyl- and so on, or combinations of substituents. According to formula (I), therefore, substituted alkyls include hydroxyalkyl, aminoalkyl, nitroalkyl, haloalkyl, alkylalkyl (branched alkyls, such as methylpentyl), (cycloalkyl)alkyl, phenylalkyl, alkoxy, alkylaminoalkyl, dialkylaminoalkyl, arylalkyl, aryloxyalkyl, arylalkyloxyalkyl, (heterocyclic radical)alkyl, and (heterocyclic radical)oxyalkyl. $R_1$ thus includes hydroxyalkyl, hydroxyalkenyl, hydroxyalkynyl, hydroxycycloalkyl, hydroxyaryl, aminoalkyl, aminoalkenyl, aminoalkynyl, aminocycloalkyl, aminoaryl, alkylalkenyl, (alkylaryl)alkyl, (haloaryl)alkyl, (hydroxyaryl)alkynyl, and so forth. Similarly, $R_A$ includes hydroxyalkyl and aminoaryt, and R$_B$ includes hydroxyalkyl, aminoalkyl, and hydroxyalkyl(heterocyclic radical)alkyl.

Heterocyclic radicals, which include but are not limited to heteroaryls, include: furyl, oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their non-aromatic counterparts. Further examples of heterocyclic radicals include piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an IC$_{50}$ for MEK 1 or MEK 2 that is at least one-fiftieth (1/50) that of its IC$_{50}$ for one of the above-named other enzymes. Preferably, a selective inhibitor has an IC$_{50}$ that is at least 1/100, more preferably 1/500, and even more preferably 1/1000, 1/5000, or less than that of its IC$_{50}$ or one or more of the above-named enzymes.

B. Compounds

One aspect of the invention features disclosed compounds shown in formulae (I) and (II) in the Summary section. Embodiments of the invention includes compounds of formula (I) wherein: (a) R$_3$ is NO$_2$; (b) R$_4$ is fluoro; (c) each of R$_3$ and R$_4$ is independently selected from H and fluoro; (d) R$_5$ is methyl, fluoro, or chloro; (e) R$_6$ is methyl, chloro, fluoro, nitro, or hydrogen; (f) R$_6$ is H; (g) R$_6$ is fluoro; (h) R$_K$ is methyl or ethyl; (i) R$_1$ is H, methyl, ethyl, propyl, isopropyl, isobutyl, benzyl, phenyl, phenethyl, allyl, C$_{3-5}$ alkenyl, C$_{3-6}$ cycloalkyl, (C$_{3-5}$ cycloalkyl)C$_{1-2}$ alkyl, (C$_{3-5}$ heterocyclic radical)C$_{1-2}$ alkyl, or (CH$_2$)$_{2-4}$ NR$_C$R$_D$; (j) R$_1$ is H or (C$_{3-4}$ cycloalkyl)C$_{1-2}$ alkyl; (k) R$_2$ is H or methyl; (l) R$_A$ has at least one hydroxyl substituent; (m) R$_A$ is H, methyl, ethyl, isobutyl, hydroxyethyl, phenyl, 2-piperidin-1-yl-ethyl, 2,3-dihydroxy-propyl, 3-[4-(2-hydroxyethyl)-piperazin-1-yl]-propyl, 2-pyrrolidin-1-yl-ethyl, or 2diethylamimo-ethyl; and R$_B$ is H; or where R$_B$ is methyl and R$_A$ is phenyl; (n) W is NR$_A$R$_B$ or NR$_2$NR$_A$R$_B$; (o) W is NR$_2$(CH$_2$)$_{2-4}$ NR$_A$R$_B$ or O(CH$_2$)$_{2-3}$ NR$_A$R$_B$; (p) W is NR$_2$OR$_1$; (q) W is OR$_B$; (r) R$_7$ is in the para position relative to X; (s) R$_7$ is iodo; (t) R$_8$ is in the ortho position relative to X; (u) or combinations thereof.

In additional embodiments, if R$_6$ is H, then R$_5$ is nitro; or R$_6$ is methyl, halo, or nitro; or R$_3$ is SO$_2$NR$_f$(CH$_2$)$_{2-4}$NR$_E$R$_F$, SO$_2$NR$_J$R$_K$ or (CO)T. In some embodiments, Ar is phenyl (e.g., formula (I)), and in other embodiments, Ar is 2-pyridyl, 3-pyridyl, or 4-pyridyl. Preferably, where one of R$_1$, R$_2$, R$_A$, R$_B$, R$_C$, and R$_D$ is an alkenyl or alkynyl group, the double or triple bond, respectively, is not adjacent the point of attachment. For example, where W is NR$_2$OR$_1$, R$_2$ is preferably prop-2-ynyl, or but-2 or 3-enyl, and less preferably prop-1-ynyl or but-1-enyl. Some embodiments include the formula 2,4-bis-(2-chloro-4-iodo-phenylamino)-3-fluoro-5-nitro-benzoic acid, the compounds in the following list, and 2-methyl (instead of 2-chloro) analogs thereof.

1. 2-(2-Chloro-4-iodo-phenylamino)-3-fluoro-5-nitro-4-(4-sulfamoyl-phenylamino)-benzoic acid
2. 2-(2-Chloro-4-iodo-phenylamino)-3-fluoro-5-nitro-4-phenylamino-benzoic acid
3. 2-(2-Chloro-4-iodo-phenylamino)-3-fluoro-5-nitro-4-phenoxy-benzoic acid
4. 2-(2-Chloro-4-iodo-phenylamino)-3-fluoro-5-nitro-4-phenylsulfanyl-benzoic acid
5. 2-(2-Chloro-4-iodo-phenylamino)-3-fluoro-4-(methyl-phenyl-amino)-5-nitro-benzoic acid
6. 2-[(2-chloro-4-iodophenyl)amino]-3-fluoro-4-[[4-[[(2-hydroxyethyl)amino]-carbonyl]phenyl]amino]-5-nitrobenzoic acid;
7. 2-[(2-chloro-4-iodophenyl)amino]-4-[[4-1(dimethylamino)carbonyl]phenyl]amino]-3-fluoro-5-nitro-benzoic acid;
8. 2-(2-Chloro-4-iodo-phenylamino)-3,5-difluoro-4-phenylamino-benzoic acid
9. 2-(2-Chloro-4-iodo-phenylamino)-3-fluoro-5-nitro-4-(3-sulfamoyl-phenylamino)-benzoic acid;
10. 2-(2-Chloro-4-iodo-phenylamino)-3-fluoro-5-nitro-4-(2-sulfamoyl-phenylamino)-benzoic acid;
11. 2-(2-Chloro-4-iodo-phenylamino)-3-fluoro-N-hydroxy-5-nitro-4-(4-sulfamoyl-phenylamino)-benzamide;
12. 2-(2-Chloro-4-iodo-phenylamino)-3-fluoro-N-hydroxy-5-nitro-4-phenylamino-benzamide;
13. 2-(2-Chloro-4-iodo-phenylamino)-3-fluoro-N-hydroxy-5-nitro4-phenoxy-benzamide;
14. 2-(2-Chloro-4-iodo-phenylamino)-3-fluoro-N-hydroxy-5-nitro4-phenylsulfanyl-benzamide;
15. 2-(2-Chloro-4-iodo-phenylamino)-3-fluoro-N-hydroxy-4-(methyl-phenyl-amino)-5-nitro-benzamide;
16. 2-[(2-chloro-4-iodophenyl)amino]-3-fluoro-N-hydroxy-4-[[4-[[(2-hydroxyethyl)amino]-carbonyl]phenyl]amino]-5-nitro-benzamide;
17. 2-[(2-chloro-4-iodophenyl)amino]4-[[4-[(dimethylamino)carbonyl]phenyl]amino]-3-fluoro-N-hydroxy-5-nitro-benzamide;
18. 2-(2-Chloro-4-iodo-phenylamino)-3,5-difluoro-N-hydroxy-4-phenylamino-benzamide;
19. 2-(2-Chloro-4-iodo-phenylamino)-3-fluoro-N-hydroxy-5-nitro4-(3-sulfamoyl-phenylamino)-benzamide;
20. 2-(2-Chloro-4-iodo-phenylamino)-3-fluoro-N-hydroxy-5-nitro4-(2-sulfamoyl-phenylamino)-benzamide;
21. 2-(2-Chloro-4-iodo-phenylamino)-N-cyclopropylmethoxy-3-fluoro-5-nitro-4-(4-sulfamoyl-phenylamino)-benzamide;
22. 2-(2-Chloro-4-iodo-phenylamino)-N-cyclopropylmethoxy-3-fluoro-5-nitro-4-phenylamino-benzamide;
23. 2-(2-Chloro-4-iodo-phenylamino)-N-cyclopropylmethoxy-3-fluoro-5-nitro-4-phenoxy-benzamide;
24. 2-(2-Chloro-4-iodo-phenylamino)-N-cyclopropylmethoxy-3-fluoro-5-nitro-4-phenylsulfanyl-benzamide;
25. 2-(2-Chloro-4-iodo-phenylamino)-N-cyclopropylmethoxy-3-fluoro-4-(methyl-phenyl-amino)-5-nitro-benzamide;
26. 2-[(2-chloro-4-iodophenyl)amino]-3-fluoro-N-cyclopropylmethoxy-4-[[4-[[(2-hydroxyethyl)amino]-carbonyl]phenyl]amino]-5-nitro-benzamide;
27. 2-[(2-chloro-4-iodophenyl)amino]4-[[4-[(dimethylamino)carbonyl]phenyl]-amino]-3-fluoro-N-cyclopropylmethoxy-5-nitro-benzamide;
28. 2-(2-Chloro-4-iodo-phenylamino)-N-cyclopropylmethoxy-3,5-difluoro-4-phenylamino-benzamide;
29. 2-(2-Chloro-4-iodo-phenylamino)-N-cyclopropylmethoxy-3-fluoro-5-nitro-4-(3-sulfamoyl-phenylamino)-benzamide; and 30. 2-(2-Chloro-4-iodo-phenylamino)-N-cyclopropylmethoxy-3-fluoro-5-nitro-4-(2-sulfamoyl-phenylamino)-benzamide.

In the scheme below, W can also be any of the values described herein for formula (I) or (II) in the section describing preferred values for W. The compound numbers provided in the scheme correspond to the numbers provided in the above list; these compounds are illustrative, not limitative, of the invention.

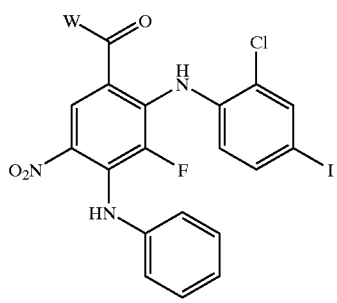

1

Cmpd # (W)
1 (OH)
11 (NHOH)
21 (NHOCH$_2$$^c$Pr)

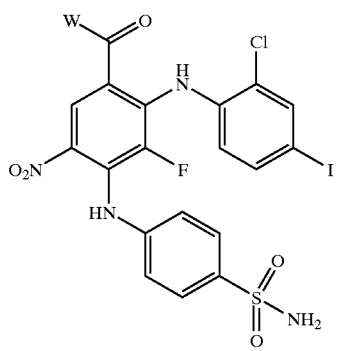

2

Cmpd # (W)
2 (OH)
12 (NHOH)
22 (NHOCH$_2$$^c$Pr)

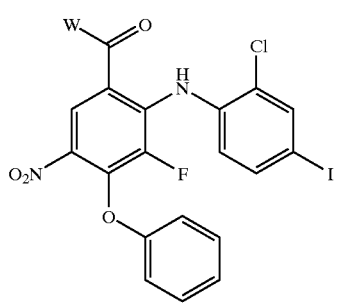

3

Cmpd # (W)
3 (OH)
13 (NHOH)
23 (NHOCH$_2$$^c$Pr)

-continued

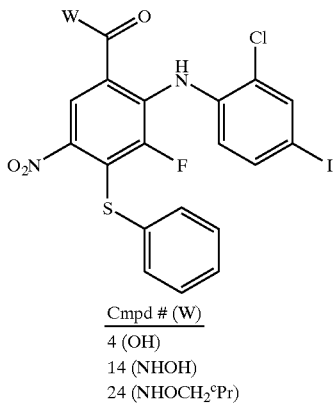

4

Cmpd # (W)
4 (OH)
14 (NHOH)
24 (NHOCH$_2$$^c$Pr)

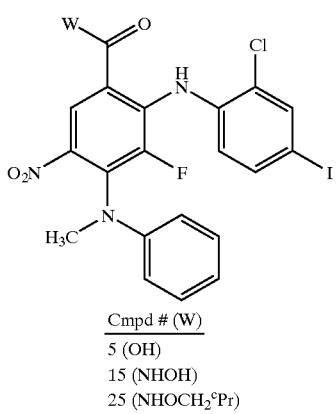

5

Cmpd # (W)
5 (OH)
15 (NHOH)
25 (NHOCH$_2$$^c$Pr)

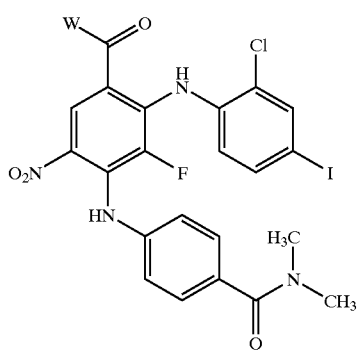

6

Cmpd # (W)
6 (OH)
16 (NHOH)
26 (NHOCH$_2$$^c$Pr)

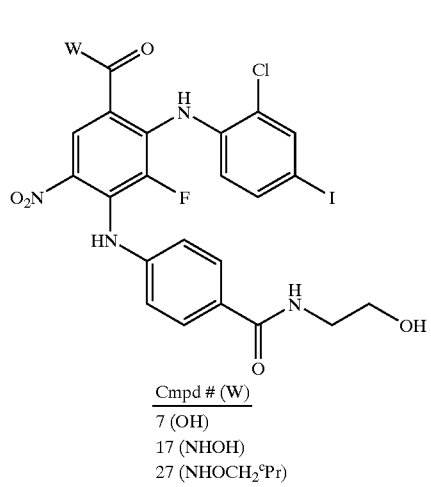

Cmpd # (W)
7 (OH)
17 (NHOH)
27 (NHOCH₂ᶜPr)

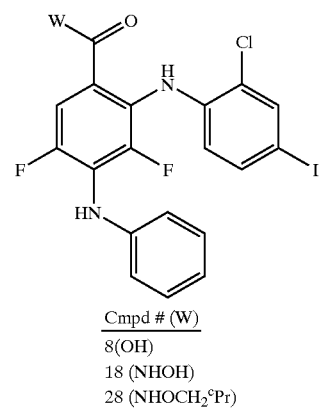

Cmpd # (W)
8(OH)
18 (NHOH)
28 (NHOCH₂ᶜPr)

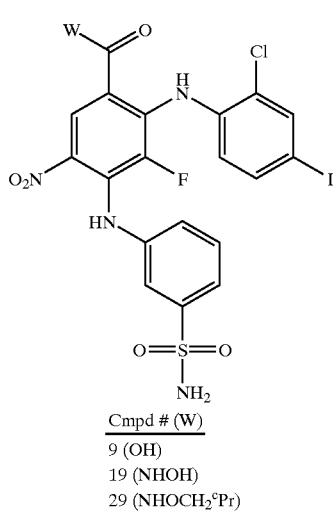

Cmpd # (W)
9 (OH)
19 (NHOH)
29 (NHOCH₂ᶜPr)

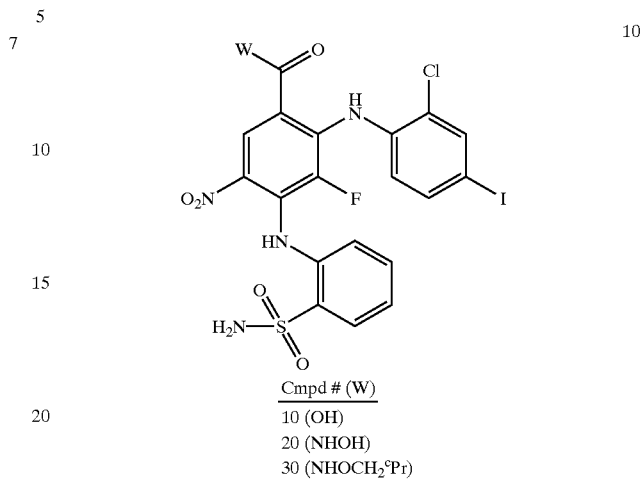

Cmpd # (W)
10 (OH)
20 (NHOH)
30 (NHOCH₂ᶜPr)

C. Synthesis

The disclosed compounds can be synthesized according to the following two Schemes, or variants thereof (see also Example 1).

Regarding the first step of synthetic Scheme 1, the reaction of the aniline and the benzoic acid derivative generally is accomplished by mixing the benzoic acid with an equimolar quantity or excess of the aniline in an unreactive organic solvent such as tetrahydrofuran, or toluene, in the presence of a base such as lithium diisopropylamide, lithium hexamethyldisilazide, n-butyl lithium, sodium hydride, or sodium amide. The reaction generally is carried out at a temperature of about −78° C. to about 25° C., and normally is complete within 2 hours to about 4 days. The product can be isolated by removing the solvent, for example by evaporation under reduced pressure, and further purified, if desired, by standard methods such as chromatography, crystallization, or distillation.

Turning to the second step, the 2-phenylamino benzoic acid derivative is next reacted with an equimolar quantity or excess of a nucleophile such as an aniline, a phenol, or a thiophenol by mixing in an unreactive organic solvent such as tetrahydrofuran, or toluene, in the presence of a base such as lithium diisopropylamide, lithium hexamethyidisilazide, n-butyl lithium, sodium hydride, or sodium amide. The reaction generally is carried out at a temperature of about −78° C. to boiling, and normally is complete within 2 hours to about 4 days. The product can be isolated by removing the solvent, for example by evaporation under reduced pressure, and further purified, if desired, by standard methods such as chromatography, crystallization, or distillation.

Finally, regarding step 3, the 4-arylheteroatom-2-phenylamino benzoic acid derivative next is reacted with a nucleophile such as ammonia, an amine, an alcohol, hydrazine, a hydrazine derivative, or a hydroxylamine derivative in the presence of a peptide coupling reagent. Amines that can be employed include monomethylamine and aniline. Alcohols that can be employed include cyclobutylmethanol and phenol. Hydrazine derivatives that can be employed include N,N-dimethylhydrazine and 1-aminopiperidine. Hydroxylamine derivatives that can be employed include methoxylamine, N-ethyl-isopropoxy amine, and tetrahydrooxazine. Typical coupling reagents include 2ethoxy-1-ethoxycarbonyl-1,2-dihydroquinoline (EEDQ), 1,3-dicyclohexylcarbodiimide (DCC), bromo-tris-(pyrrolidino)-phosphonium hexafluorophosphate (PyBrOP) and (benzotriazolyloxy) tripyrrolidino phosphonium hexafluorophosphate (PyBOP). The 4-arylheteroatom-2-phenylamino benzoic acid derivative and the nucleophile normally are mixed in approximately equimolar quantities in an unreactive solvent such as dichloromethane, tetrahydrofuran, chloroform, or xylene, and an equimolar quantity of the coupling reagent is added. A base such as triethylamine or diisopropylethylamine can be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone diethyl ether or ethanol.

Referring to synthetic Scheme 2, an alternative method for making the compounds of the invention involves first coupling the benzoic acid derivative with the arylheteroatom nucleophile, and then reacting this 4-arylheteroatom benzoic acid derivative with an aniline. The final step involves the coupling of the 4-arylheteroatom-2-phenylamino benzoic acid derivative with the ammonia, amine, alcohol, hydrazine, hydrazine derivative, or hydroxylamine derivative with a peptide coupling reagent. The general reaction conditions for all of the steps in Scheme 2 are similar to those described above for synthetic Scheme 1.

Scheme 1

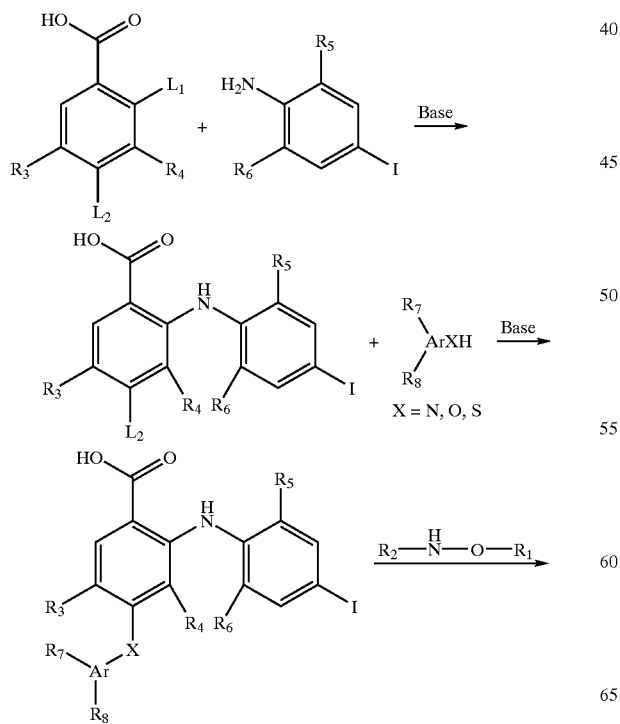

Scheme 2

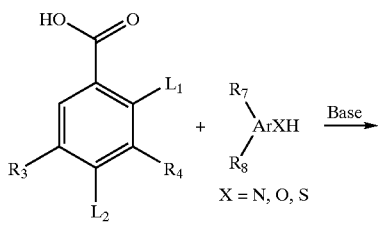

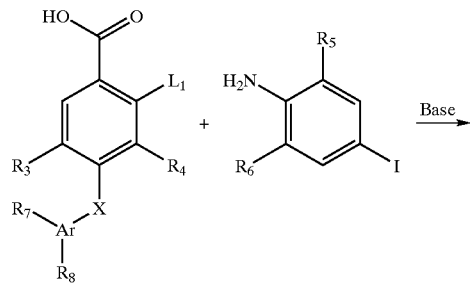

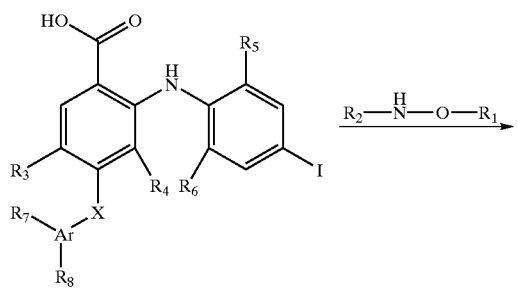

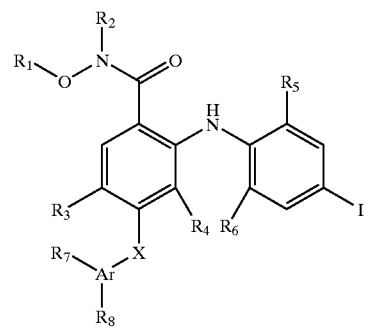

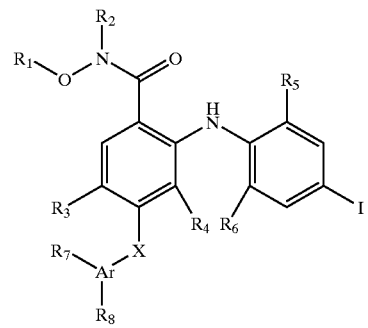

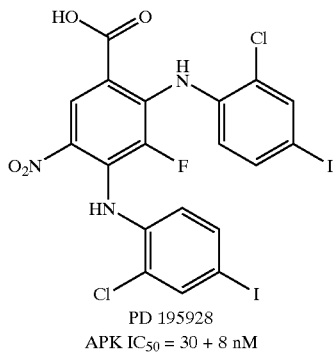

PD 195928
APK IC$_{50}$ = 30 + 8 nM

D. Uses

The disclosed compositions are useful as both prophylactic and therapeutic treatments for diseases or conditions as provided in the Summary section, as well as diseases or conditions modulated by the MEK cascade. Examples include stroke, heart failure, osteoarthritis, rheumatoid arthritis, organ transplant rejection, and a variety of tumors such as ovarian, lung, pancreatic, and colon.

1. Dosages

Those skilled in the art will be able to determine, according to known methods, the appropriate dosage for a patient, taking into account factors such as age, weight, general health, the type of pain requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight. Commercially available capsules or other formulations (such as liquids and film-coated tablets) of 100 mg, 200 mg, 300 mg, or 400 mg can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Related compounds

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic), amino acid addition salts, esters, and amides which are within a reasonable benefit/risk ratio, pharmacologically effective, and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See, for example, S. M. Berge, et al., "Pharmaceutical Salts," *J. Pharm. Sci.*, 1977, 66:1–19 which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., hydroxyl, amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention.

HYDROXYL PROTECTING GROUPS

Hydroxyl protecting groups include: ethers, esters, and protection for 1,2- and 1,3-diols. The ether protecting groups include: methyl, substituted methyl ethers, substituted ethyl ethers, substituted benzyl ethers, silyl ethers and conversion of silyl ethers to other functional groups.

Substituted Methyl Ethers

Substituted methyl ethers include: methoxymethyl, methylthiomethyl, t-utylthiomethyl, (phenyidimethylsilyl) methoxymethyl, benzyloxymethyl, p-ethoxybenzyloxymethyl, (4-methoxyphenoxy) methyl, guaiacolmethyl, t-butoxymethyl, 4-pentenyloxymethyl, siloxymethyl, 2-methoxyethoxymethyl, 2,2,2-trichloroethoxymethyl, bis(2-chloro-ethoxy)methyl, 2-(trimethylsilyl)ethoxymethyl, tetrahydropyranyl, 3-bromotetrahydro-pyranyl, tetrahydrothiopyranyl, 1-methoxycyclohexyl, 4-methoxytetrahydropyranyl, 4-methoxytetrahydrothio-pyranyl, 4-methoxytetrahydrothiopyranyl S,S-dioxido, 1-[(2-chloro- 4-methyl)phenyl]4-methoxypiperidin-4-yl, 1,4-dioxan-2-yl, tetrahydrofuranyl, tetrahydrothiofuranyl, and 2,3,3a,4,5,6,7, 7a-octahydro-7,8,8-trimethyl-4,7-ethanobenzofuran-2-yl.

Substituted Ethyl Ethers

Substituted ethyl ethers include: 1-ethoxyethyl, 1-(2, chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilyethyl, 2-(phenylselenyl)ethyl, t-butyl, allyl, p-chlorophenyl, p-methoxyphenyl, 2,4-dinitrophenyl, and benzyl.

Substituted Benzyl Ethers

Substituted benzyl ethers include: p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'dinitrobenzhydryl, 5-dibenzosuberyl, triphenylmethyl, α-naphthyidiphenylmethyl, p-methoxyphenyldiphenylmethyl, di(p-methoxyphenyl) phenylmethyl, tri-(p-methoxyphenyl)methyl, 4-(4'-bromophenacyloxy)phenyldiphenylmethyl, 4,4',4"-tris(4,5-dichlorophthalimido-phenyl)methyl, 4,4',4"-tris (levulinoyloxyphenyl) methyl, 4,4', 4"tris(benzoyloxphenyl)methyl, 3-(imidazol-1-ylmethyl)bis(4',4"-dimethoxyphenyl)-methyl, 1,1-bis(4-methoxyphenyl)-1'-pyrenylmethyl, 9-anthryl, 9-(9-phenyl) xanthenyl, 9-(9-phenyl-10-oxo) anthryl, 1,3-benzodithiolan-2-yl, and benzisothiazolyl S,S-dioxido.

Silyl Ethers

Silyl ethers include: trimethylsilyl, triethylsilyl, triisopropylsilyl, dimethylisopropylsilyl, diethylisopropylsilyl, dimethylthexylsilyl, t-butyldimethylsilyl, t-butyidiphenylsilyi, tribenzylsilyl, tri-p-xylylsilyl, triphenylsilyl, diphenylmethylsilyl, and t-butylmethoxyphenylsilyl.

ESTERS

Esters protecting groups include: esters, carbonates, assisted cleavage, miscellaneous esters, and sulfonates.

Esters

Examples of protective esters include: formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio) pentanoate, pivaloate, adamantoate, crotonate, 4-methoxycrotonate, benzoate, p-phenylbenzoate, and 2,4,6-trimethylbenzoate (mesitoate).

Carbonates

Carbonates include: methyl, 9-fluorenylmethyl, ethyl, 2,2, 2-trichloroethyl, 2-(trimethylsilyl) ethyl, 2-(phenylsulfonyl) ethyl, 2-(triphenylphosphonio) ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage protecting groups include: 2-iodobenzoate, 4-azido-butyrate, 4-nitro-4-methylpentanoate, o-(dibromomethyl) benzoate, 2-formylbenzene-sulfonate, 2-(methylthiomethoxy) ethyl carbonate, 4-(methylthio-methoxymethyl) benzoate, and 2-(methylthiomethoxymethyl) benzoate.

Miscellaneous Esters

In addition to the above classes, miscellaneous esters include: 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate (tigloate), o-(methoxycarbonyl) benzoate, p-P-benzoate, α-naphthoate, nitrate, alkyl N,N, N'N'-tetramethylphosphorodiamidate, N-phenylcarbamate, borate, dimethylphosphinothioyl, and 2,4-dinitrophenylsulfenate.

Sulfonates

Protective sulfates includes; sulfate, methanesulfonate (mesylate), benzylsulfonate, and tosylate.

PROTECTION FOR 1,2- AND 1,3-DIOLS

The protection for 1,2 and 1,3-diols group includes: cyclic acetals and ketals, cyclic ortho esters, and silyl derivatives.

Cyclic Acetals and Ketals

Cyclic acetals and ketals include: methylene, ethylidene, 1-t-butylethylidene, 1-phenylethylidene, (4-methoxyphenyl) ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Cyclic ortho esters include: methoxymethylene, ethoxymethylene, dimethoxy-methylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino) benzylidene derivative, and 2-oxacyclopentylidene.

PROTECTION FOR THE CARBOXYL GROUP ESTERS

Ester protecting groups include: esters, substituted methyl esters, 2-substituted ethyl esters, substituted benzyl esters, silyl esters, activated esters, miscellaneous derivatives, and stannyl esters.

Substituted Methyl Esters

Substituted methyl esters include: 9-fluorenylmethyl, methoxymethyl, methylthiomethyl, tetrahydropyranyl, tetrahydrofuranyl, methoxyethoxymethyl, 2-(trimethylsilyl) ethoxy-methyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

2-Substituted ethyl esters include: 2,2,2-trichloroethyl, 2-haloethyl, 1-chloroalkyl, 2-(trimethylsily)ethyl, 2-methylthioethyl, 1,3-dithianyl-2-methyl, 2(p-nitrophenylsulfenyl)-ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsily)-2-buten-1-yl, cinnamyl, α-methylcinnamyl, phenyl, p-(methylmercapto)-phenyl, and benzyl.

Substituted Benzyl Esters

Substituted benzyl esters include: triphenylmethyl, diphenylmethyl, bis(o-nitrophenyl)methyl, 9-anthrylmethyl, 2-(9,10-dioxo)anthrylmethyl, 5-dibenzo-suberyl, 1-pyrenylmethyl,2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, and 4-P-benzyl.

Silyl Esters

Silyl esters include: trimethylsilyl, triethylsilyl, t-butyldimethylsilyl, i-propyldimethylsilyl, phenyidimethylsilyl, and di-t-butylmethylsilyl.

Miscellaneous Derivatives

Miscellaneous derivatives includes: oxazoles, 2-alkyl-1,3-oxazolines, 4-alkyl-5-oxo-1,3-oxazolidines, 5-alkyl-4-oxo-1,3-dioxolanes, ortho esters, phenyl group, and pentaaminocobalt(III) complex.

Stannyl Esters

Examples of stannyl esters include: triethylstannyl and tri-n-butylstannyl.

AMIDES AND HYDRAZIDES

Amides include: N,N -dimethyl, pyrrolidinyl, piperidinyl, 5,6-dihydrophen-anthridinyl, o-nitroanilides, N-7-nitroindolyl, N-8-nitro-1,2,3,4-tetrahydroquinolyl, and p-P-benzenesulfonamides. Hydrazides include: N-phenyl, N,N'-diisopropyl and other dialkyl hydrazides.

PROTECTION FOR THE AMINO GROUP CARBAMATES

Carbamates include: carbamates, substituted ethyl, assisted cleavage, photolytic cleavage, urea-type derivatives, and miscellaneous carbamates.

Carbamates

Carbamates include: methyl and ethyl, 9-fluorenylmethyl, 9-(2-sulfo)fluorenyl-methyl, 9-(2,7-dibromo)fluorenylmethyl, 2,7-di-t-butyl-[9-(10,10-dioxo-10,10,10,10-tetrahydro-thioxanthyl)]methyl, and 4-methoxyphenacyl.

Substituted Ethyl

Substituted ethyl protective groups include: 2,2,2-trichloroethyl, 2-trimethylsilylethyl, 2-phenylethyl, 1-(1-adamantyl)-1-methylethyl, 1,1-dimethyl-2-haloethyl, 1,1dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'-and 4'-pyridyl)ethyl, 2-(N,N-icyclohexylcarboxamido)-ethyl, t-butyl, 1-adamantyl, vinyl, allyl, 1-isopropylallyl, connamyl, 4-nitrocinnamyl, quinolyl, N-hydroxypiperidinyl, alkyldithio, benzyl, p-methoxybenzyl, p-nitrobenzyl, p-bromobenzyl, p-chlorobenzyl, 2,4dichlorobenzyl, 4-methylsulfinylbenzyl, 9-anthrylmethyl, and diphenylmethyl.

Assisted Cleavage

Protection via assisted cleavage includes: 2-methylthioethyl, 2-methylsulfonylethyl, 2-(p-toluenesulfonyl)ethyl, [2-(1,3-dithianyl)]methyl, 4-methylthiophenyl, 2,4-dimethyl-thiophenyl, 2-phosphonioethyl, 2-triphenylphosphonioisopropyl, 1,1-dimethyl-2cyanoethyl, m-chloro-p-acyloxybenzyl, p(dihydroxyboryl)benzyl, 5-benzisoxazolyl-methyl, and 2-(trifluoromethyl)-6-chromonylmethyl.

Photolytic Cleavage

Photolytic cleavage methods use groups such as: m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of of urea-type derivatives include: phenothiazinyl-(10)-carbonyl derivative,N'-p-toluenesulfonylaminocarbonyl, and N'-phenylaminothiocarbonyl.

Miscellaneous Carbamates

In addition to the above, miscellaneous carbamates include: t-amyl, S-benzyl thiocarbamate, p-cyanobenzyl, cyclobutyl, cyclohexyl, cyclopentyl, cyclopropylmethyl, p-decyloxy-benzyl, diisopropylmethyl, 2,2-dimethoxycarbonylvinyl, o-(N,N-dimethyl-carboxamido)-benzyl, 1,1-dimethyl-3(N,N-dimethylcarboxamido)propyl, 1,1-dimethyl-propynyl, di(2-pyridyl)methyl, 2-furanylmethyl, 2-iodoethyl, isobornyl, isobutyl, isonicotinyl, p(p'-methoxyphenylazo)benzyl, 1-methylcyclobutyl, 1-methylcyclohexyl, 1-methyl-1-cyclopropylmethyl, 1-methyl-(3,5-dimethoxyphenyl)ethyl, 1-methyl-1(p-henylazophenyl)-ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

AMIDES

Amides

Amides includes: N-formyl, N-acetyl, N-chloroacetyl, N-trichloroacetyl, N-trifluoroacetyl, N-phenylacetyl, N-3-phenylpropionyl, N-picolinoyl, N-3-pyridyl-carboxamide, N-benzoylphenylalanyl derivative, N-benzoyl, and N-p-phenylbenzoyl.

Assisted Cleavage

Assisted cleavage groups include: N-o-nitrophenylacetyl, N-o-nitrophenoxyacetyl, N-acetoacetyl, (N'-dithiobenzyloxycarbonylamino)acetyl, N-3-(phydroxphenyl) propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3methyl-3-nitrobutyryl, N-o-nitrocinnamoyl, N-acetylmethionine derivative, N-o-nitrobenzoyl, N-o-(benzoyloxymethyi)benzoyl, and 4,5-diphenyl-3-oxazolin-2-one.

Cyclic Imide Derivatives

Cyclic imide derivatives include: N-phthalimide, N-dithiasuccinoyl, N-2,3-diphenyl-maleoyl, N-2,5-dimethylpyrrolyl, N-1,1,4,4-tetramethyidisilylazacyclopentane adduct, 5-substituted 1,3- dimethyl-1,3,5-triazacyclohexan-2-one, 5-substituted 1,3-dibenzyl-1,3,5-triazacyclohexan-2-one, and 1-substituted 3,5-dinitro-4-pyridonyl.

SPECIAL -NH PROTECTIVE GROUPS

Protective groups for —NH include: N-alkyl and N-aryl amines, imine derivatives, enamine derivatives, and N-hetero atom derivatives (such as N-metal, N—N, N—P, N—Si, and N—S), N-sulfenyl, and N-sulfonyl.

N-Alkyl and N-Aryl Amines

N-alkyl and N-aryl amines include: N-methyl, N-allyl, N-[2-(trimethylsilyl)ethoxyl]-methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

Imine derivatives include: N-1,1-dimethylthiomethylene, N-benzylidene, N-p-methoxybenzylidene, N-diphenylmethylene, N-[(2-pyridyl)mesityl]methylene, N-(N',N'-dimethylaminomethylene), N,N'-isopropylidene, N-p-nitrobenzylidene, N-salicylidene, N-5-chlorosalicylidene, N-(5-chloro-2-hydroxyphenyl)phenylmethylene, and N-cyclohexylidene.

Enamine Derivative

An example of an enamine derivative is N-(5,5-dimethyl-3-oxo-1-cyclohexenyl).

N-Hetero Atom Derivatives

N-metal derivatives include: N-borane derivatives, N-diphenylborinic acid derivative, N-[phenyl (pentacarbonylchromium- or -tungsten)]carbenyl, and N-copper or N-zinc chelate. Examples of N-N derivatives include: N-nitro, N-nitroso, and N-oxide. Examples of N-P derivatives include: N-diphenylphosphinyl, N-dimethylthiophosphinyl, N-diphenylthiophosphinyl, N-dialkyl phosphoryl, N-dibenzyl phosphoryl, and N-diphenyl phosphoryl. Examples of N-sulfenyl derivatives include: N-benzenesulfenyl, N-o-nitrobenzenesulfenyl, N-2,4-dinitrobenzenesulfenyl, N-pentachlorobenzenesulfenyl, N-2-nitro4-methoxy-benzenesulfenyl, N-triphenylmethylsulfenyl, and N-3-nitropyridinesulfenyl. N-sulfonyl derivatives include: N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl4-methoxybenzenesulfonyl, N-pentamethylbenzenesulfonyl, N-2,3,5,6-tetramethyl4-methoxybenzene-sulfonyl, N4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilylethanesulfonyl, N-9-anthracenesulfonyl, N-4-(4',8'-dimethoxynaphthylmethyl)-benzenesulfonyl, N-benzylsulfonyl, N-trifluoromethylsulfonyl, and N-phenacylsulfonyl.

Disclosed compounds which are masked or protected may be prodrugs, compounds metabolized or otherwise transformed in vivo to yield a disclosed compound, e.g., transiently during metabolism. This transformation may be a hydrolysis or oxidation which results from contact with a bodily fluid such as blood, or the action of acids, or liver, gastrointestinal, or other enzymes.

Features of the invention are further described in the examples below.

E. Examples

EXAMPLE 1

Preparation of 2.4-bis-(2-Chloro-4-iodo-phenylamino)-3-fluoro-5-nitrobenzoic Acid Step a: Preparation of 5-Nitro-2,3,4-trifluorobenzoic Acid To gently stirring concentrated sulfuric acid (50 ml) was added fuming nitric acid (3.4 ml, 0.076 mol). Solid 2,3,4-trifluorobenzoic acid (10.00 g, 0.05565 mol) was added directly in increments. After stirring 45 minutes, the reaction mixture had become an orange homogeneous solution which was then poured over chilled water (400 ml). The resulting aqueous suspension was extracted with diethyl ether (3×200 ml). The combined extracts were dried with anhydrous magnesium sulfate and concentrated in vacuo to yield 12.30 g of a dull, light-yellow solid. Recrystallization from chloroform (50 ml) afforded 9.54 g of the pale yellow microcrystalline product; 78% yield; m.p.; $^1$H-NMR (400 MHz; DMSO) δ14.29 (broad s, 1H), 8.43–8.38 (m, 1H); $^{13}$C-NMR (100 MHz; DMSO) δ162.41, 154.24 (dd, $J_{C-F}$=270.1, 10.7 Hz), 148.35 (dd, $J_{C-F}$=267.0, 9.2 Hz), 141.23 (dt, $J_{C-F}$=253.4 Hz), 133.95, 123.30 (d, $J_{C-F}$=2.2 Hz), 116.92 (dd, $J_{C-F}$=18.2, 3.8 Hz); $^{19}$F-NMR (376 MHz; DMSO) δ–120.50 to –120.63 (m), –131.133 to –131.27 (m), –153.63 to –153.74 (m).

Step b: Preparation of 2,4-bis-(2-Chloro-4-iodo-phenylamino)-3-fluoro-5-Nitrobenzoic Acid To a stirring solution comprised of 2-chloro-4-iodoaniline (Lancaster, 98%, 12.33 g, 0.04864 mol) in tetrahydrofuran (20 ml) at –78° C. under nitrogen was added a 2.0 M lithium diisopropylamide solution in tetrahydrofuran-heptane-ethylbenzene (Aldrich, 35 ml, 0.070 mol) with a syringe. The addition formed a thick suspension. After five minutes of stirring, a solution comprised of 5-nitro-2,3,4-trifluorobenzoic acid (5.00 g, 0.0226 mol) in tetrahydrofuran (30 ml) was added with a syringe to give a dark reaction mixture. The cold bath was removed and the reaction mixture stirred for 20 minutes. The cool reaction mixture was poured into ether (600 ml) containing an excess of hydrogen chloride. The red solution instantly turned to a yellow suspension as a precipitate formed. This precipitate was removed by vacuum filtration. The filtrate was concentrated in vacuo to a red powder (10.5 g). The red powder was triturated with boiling chloroform (800 ml). The triturated solids were collected by vacuum filtration to give an orange powder (2.42 g). The mother liquor from the trituration was concentrated in vacuo to give a red-orange solid (ca. 10 g undried). This solid was loaded onto a flash silica column. Elution with dichloromethane removed some impurities. Continuing elution with 1% methanol in dichloromethane afforede ca. 4 g of a red solid. This red solid was dissolved in hot absolute ethanol (100 ml). The solution was boiled down to 50 ml before dilution to 300 ml with hexanes. This solution was boiled to 150 ml and rediluted to 300 ml with hexanes to produce slight turbidity. The mixture was cooled in the refrigerator for three days, affording a yellow precipitate. The precipitate was collected by vacuum filtration and was dried with suction to afford 0.15 g of a yellow solid; 1% yield; $^1$H-NMR (400 MHz; DMSO) δ 8.94 (s, 1H), 8.55 (s, 1H), 7.79 (d, 2H, J=2.0 Hz), 7.61–7.57 (m, 2H), 6.90 (dd, 1 H, J=8.5, 3.9 Hz), 6.84 (dd, 1H, J=8.3, 6.6 Hz); $^{19}$F-NMR (376 MHz; DMSO) δ–122.62 (s); MS (APCI+) 692 (6), 691

(8), 690 (31), 689 (10), 688 (55), 171 (47), 130 (100); (APCI−) 691 (4), 690 (12), 689 (14), 688 (70), 687 (32), 686 (100), 506 (50), 453 (97); IR (KBr) 1523 cm$^{-1}$; Anal. calcd/found for: $C_{19}H_{10}Cl_2Fl_2N_3O_4$ C, 33.17/33.32; H, 1.47/1.73; N, 6.11/5.73; Cl 10.31/10.04; F, 2.76/3.70; I, 36.89134.32.

The APK $IC_{50}$ for 2,4-bis-(2-chloro-4-iodo-phenylamino)-3-fluoro-5-nitrobenzoic acid is 29.6 nM.

EXAMPLE 2

Cascade Assay for Inhibitors of the MAP Kinase Pathway

Incorporation of $^{32}p$ into myelin basic protein (MBP) is assayed in the presence of a glutathione S-transferase fusion protein containing p44MAP kinase (GST-MAPK) and a glutathione S-transferase fusion protein containing p45MEK (GST-MEK). The assay solution contains 20 mM HEPES, pH 7.4, 10 mM $MgCl_2$, 1 mM $MnCl_2$, 1 mM EGTA, 50, $\mu$M [$\gamma$-$^{32}P$]ATP, 10 $\mu$g GST-MEK, 0.5 $\mu$g GST-MAPK and 40 $\mu$g MBP in a final volume of 100 $\mu$L. Reactions are stopped after 20 minutes by addition of trichloroacetic acid and filtered through a GF/C filter mat. $^{32}p$ retained on the filter mat is determined using a 120S Betaplate. Compounds are assessed at 10 $\mu$M for ability to inhibit incorporation of $^{32}p$.

To ascertain whether compounds are inhibiting GST-MEK or GST MAPK, two additional protocols are employed. In the first protocol, compounds are added to tubes containing GST-MEK, followed by addition of GST-MAPK, MBP and [$\gamma$-$^{32}P$]ATP. In the second protocol, compounds are added to tubes containing both GST-MEK and GST-MAPK, followed by MBP and [$\gamma$-$^{32}P$]ATP.

Compounds that show activity in both protocols are scored as MAPK inhibitors, while compounds showing activity in only the first protocol are scored as MEK inhibitors.

EXAMPLE 3

In Vitro MAP Kinase Assay

Inhibitory activity can be confirmed in direct assays. For MAP kinase, 1 $\mu$g GST-MAPK is incubated with 40 $\mu$g MBP for 15 minutes at 30° C. in a final volume of 50 $\mu$L containing 50 mM Tris (pH 7.5), 10 $\mu$M $MgCl_2$, 2 $\mu$M EGTA, and 10 $\mu$M [$\gamma$-$^{32}P$]ATP. The reaction is stopped by addition of Laemmli SDS sample buffer and phosphorylated MBP resolved by electrophoresis on a 10% polyacrylamide gel. Radioactivity incorporated into MBP is determined by both autoradiography, and scintillation counting of excised bands.

EXAMPLE 4

In Vitro MEK Assay

For evaluation of direct MEK activity, 10 $\mu$g GST-MEK$_1$ is incubated with 5 $\mu$g of a glutathione S-transferase fusion protein containing p44MAP kinase with a lysine to alanine mutation at position 71 (GST-MAPK-KA). This mutation eliminates kinase activity of MAPK, so only kinase activity attributed to the added MEK remains. Incubations are 15 minutes at 30° C. in a final volume of 50 $\mu$L containing 50 mM Tris (pH 7.5), 10 $\mu$M $MgCl_2$, 2, $\mu$M EGTA, and 10 $\mu$M [$\gamma$-$^{32}P$]ATP. The reaction is stopped by addition of Laemrnli SDS sample buffer. Phosphorylated GST-MAPK-KA is resolved by electrophoresis on a 10% polyacrylamide gel. Radioactivity incorporated into GST-MAPK-KA is determined by autoradiography, and subsequent scintillation counting of excised bands. Additionally, an artificially activated MEK containing serine to glutamate mutations at positions 218 and 222 (GST-MEK-2E) is used. When these two sites are phosphorylated, MEK activity is increased. Phosphorylation of these sites can be mimicked by mutation of the serine residues to glutamate. For this assay, 5 $\mu$g GST-MEK-2E is incubated with 5 $\mu$g GST-MAPK-KA for 15 minutes at 30° C. in the same reaction buffer as described above. Reactions are terminated and analyzed as above.

EXAMPLE 5

Whole Cell MAP Kinase Assay

To determine if compounds block activation of MAP kinase in whole cells, the following protocol is used. Cells are plated in multi-well plates and grown to confluence. Cells are serum-deprived overnight. Cells are exposed to the desired concentrations of compound or vehicle (DMSO) for 30 minutes, followed by addition of a growth factor, for example, PDGF (100 ng/mL). After a 5-minute treatment with the growth factor, cells are washed with PBS, and lysed in a buffer consisting of 70 mM NaCl, 10 mM HEPES (pH 7.4), 50 mM glycerol phosphate, and 1% Tritonx-100. Lysates are clarified by centrifugation at 13,000×g for 10 minutes. Five micrograms of the resulting supernatants are incubated with 10 $\mu$g microtubule associated protein-2 (Map2) for 15 minutes at 30° C. in a final volume of 25 $\mu$L containing 50 mM Tris (pH 7.4), 10 mM $MgCl_2$, 2 mM EGTA and 30 $\mu$M [$\gamma$-$^{32}P$]ATP. Reactions are terminated by addition of Laemrnli sample buffer. Phosphorylated Map2 is resolved on 7.5% acrylamide gels and incorporated radioactivity is determined by scintillation counting of excised bands.

EXAMPLE 6

Monolayer Growth

Cells are plated into multi-well plates at 10 to 20,000 cells/mL. Forty-eight hours after seeding, test compounds are added to the cell growth medium and incubation is continued for 2 additional days. Cells are then removed from the wells by incubation with trypsin and enumerated with a Coulter counter.

EXAMPLE 7

Growth in Soft-agar

Cells are seeded into 35-mm dishes at 5 to 10,000 cells/dish using growth medium containing 0.3% agar. After chilling to solidify the agar, cells are transferred to a 37° C. incubator. After 7 to 10 days' growth. visible colonies are manually enumerated with the aid of a dissecting microscope.

EXAMPLE 8

Collagen-Induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 $\mu$g type II collagen, which is a major component of joint cartilage, delivered intradermally in Freund's complete adjuvant. The disease susceptibility is regulated by the class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (stage 1), joint distortion (stage 2), to joint ankylosis (stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type II collagen, and there is a marked cellular response to CII.

EXAMPLE 9

SCW-induced Monoarticular Arthritis

Arthritis is induced as described by Schwab, et al. ,Infection and Immunity 59:4436–4442 (1991)) with minor modifications. Rats receive 6 μg sonicated SCW [in 10 μl Dulbecco's PBS (DPBS)] by an intraarticular injection into the right tibiotalar joint on day 0. On day 21, the DTH is initiated with 100 μg of SCW (250 μl) administered i.v. For oral compound studies, compounds are suspended in vehicle (0.5% hydroxypropyl-methylcellulose/0.2% Tween 80), sonicated, and administered twice daily (10 ml/kg volume) beginning 1 hr prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on day 21, and comparing them with volumes at subsequent time points such as day 22, 23, 24, and 25. Paw volume is determined by mercury plethysmography.

EXAMPLE 10

Mouse Ear-heart Transplant Model

Fey, T. A. et aL describe methods for transplanting split-heart neonatal cardiac grafts into the ear pinna of mice and rats (J. Pharm. and Toxic. Meth. 39:9–17 (1998)). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice or three times daily from the day of transplant (day 0) through day 13 or until grafts have been rejected. Rats are dosed once, twice, or three times daily from day 0 through day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10–20-fold magnification with a stereoscopic dissecting microscope without anesthesia. Recipients whose grafts are not visibly beating may be anesthetized and evaluated for the presence of electrical activity using Grass E-2 platinum subdermal pin microelectodes placed either in the pinna or directly into the graft and a tachograph. Implants can be examined 1–4 times a day for 10, 20, 30 or more days. The ability of a test compound to ameliorate symptoms of transplant rejection can be compared with a control compound such as cyclosporine, tacrolimus, or orally-administered lefluonomide.

EXAMPLE 11

Murine Ovalbumin-induced Eosinophilia

Female C57BL/6 mice are obtained from the Jackson Laboratory (Bar Harbor, Me.). All animals are given food and water ad libitum. Mice are sensitized with a single i.p. injection of OVA (grade V, Sigma Chemical Company, St. Louis, Mo.) adsorbed to alum, (10 μg OVA+9 mg alum in 200 μl saline) or vehicle control, (9 mg alum in 200 μl saline) on day 0. On day 14, the mice are challenged with a 12-minute inhalation of an aerosol consisting of 1.5% OVA (weight/volume) in saline produced by a nebulizer (small particle generator, model SPAG-2; ICN Pharmaceuticals, Costa Mesa, Calif.). Groups of eight mice are dosed with oral vehicle (0.5% hydroxypropylmethylcellulose/0.25% TWEEN-80), or a test compound at 10, 30, or 100 mg/kg in oral vehicle, 200 μl per mouse p.o. Dosing is performed once per day starting on day 7 or day, and extending through day 16.

For determination of pulmonary eosinophilia, three days after the first OVA aerosol challenge (day 17), the mice are anesthetized with an i.p. injection of anesthetic (Ketamine/Acepromazine/Xylazine), and the tracheae is exposed and cannulated. The lungs and upper airways are lavaged twice with 0.5 ml of cold PBS. A portion (200 μl) of the bronchoalveolar lavage (BAL) fluid is enumerated using a Coulter counter Model ZB1(Coulter Electronics, Hialeah, Fla.). The remaining BAL fluid is then centrifuged at 300×g for five minutes, and the cells are resuspended in 1 ml of HBSS (Gibco BRL) containing 0.5% fetal calf serum (HyClone) and 10 mM HEPES (Gibco BRL). The cell suspension is centrifuged in a cytospin (Shandon Southern Instruments, Sewickley, Pa.) and stained by Diff Quick (American Scientific Products, McGraw Park, Ill.) to differentiate BAL leukocytes into neutrophil, eosinophil, monocyte or lymphocyte subsets. The number of eosinophils in the BAL fluid is determined by multiplying the percentage of eosinophils by the total cell count.

F. Other Embodiments

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or an ester, pharmaceutical salt, hydrate, acid, or amide of a disclosed compound. Publications cited herein are hereby incorporated by reference in their entirety.

What is claimed is:
1. A compound having the formula (II):

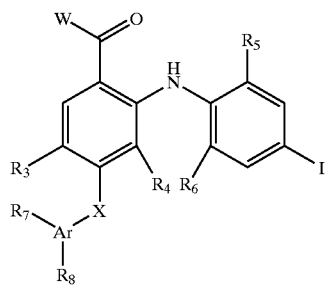

(II)

W is $OR_1$, $NR_2OR_1$, $NR_AR_B$, $NR_2NR_AR_B$, or $NR_2(CH_2)_{2-4}NR_AR_B$;

$R_1$ is H, $C_{1-8}$ alkyl, $C_{3-8}$ alkenyl, $C_{3-8}$ alkynyl, $C_{3-8}$ cycloalkyl, phenyl, (phenyl)$C_{1-4}$ alkyl, (phenyl)$C_{3-4}$ alkenyl, (phenyl)$C_{3-4}$ alkynyl, ($C_{3-8}$ cycloalkyl)-$C_{1-4}$ alkyl, ($C_{3-8}$ cycloalkyl)$C_{3-4}$ alkenyl, ($C_{3-8}$ cycloalkyl) $C_{3-4}$ alkynyl, $C_{3-8}$ heterocyclic radical, ($C_{3-8}$ heterocyclic radical)$C_{1-4}$ alkyl, ($C_{3-8}$ heterocyclic radical)$C_{3-4}$ alkenyl, ($C_{3-8}$ heterocyclic radical)$C_{3-4}$ alkynyl or $(CH_2)_{2-4}NR_AR_B$;

$R_2$ is H, phenyl, $C_{1-4}$ alkyl, $C_{3-4}$ alkenyl, $C_{3-8}$ alkynyl, $C_{3-8}$ cycloalkyl, or ($C_{3-8}$ cycloalkyl)-$C_{1-4}$ alkyl;

$R_A$ is H, $C_{1-6}$ alkyl, $C_{3-8}$ alkenyl, $C_{3-8}$ alkynyl, $C_{3-8}$ cycloalkyl, phenyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical) $C_{1-4}$ alkyl, (aminosulfonyl)phenyl, [(aminosulfonyl) phenyl]$C_{1-4}$ alkyl, (aminosulfonyl)$C_{1-6}$ alkyl, (aminosulfonyl)$C_{3-6}$ cycloalkyl, or [(aminosulfonyl) $C_{3-6}$ cycloalkyl]$C_{1-4}$ alkyl;

$R_B$ is H, $C_{1-8}$ alkyl, $C_{3-8}$ alkenyl, $C_{3-8}$ alkynyl, $C_{3-8}$ cycloalkyl, or $C_{6-8}$ aryl;

$R_3$ is halo, $NO_2$, $SO_2NR_I(CH_2)_{2-4}NR_ER_F$, $SO_2NR_IR_K$ or (CO)T;

T is $C_{1-8}$ alkyl, $C_{3-8}$ cycloalkyl, $(NR_ER_F)C_{1-4}$ alkyl, $OR_F$, $NR_I(CH_2)_{2-4}NR_ER_F$, or $NR_ER_F$;

$R_4$ is H or F;

$R_5$ is H, methyl, halo, or $NO_2$;

$R_6$ is H, methyl, halo, or $NO_2$;

Ar is phenyl, 2-pyridyl, 3-pyridyl, or 4-pyridyl;

each of $R_7$ and $R_8$ is independently selected from H, halo, $C_{1-4}$ alkyl, $SO_2NR_I(CH_2)_{2-4}NR_GR_H$, $(CO)(CH_2)_{2-4}NR_GR_H$, $(CO)NR_I(CH_2)_{2-4}NR_GR_H$, $(CO)O(CH_2)_{2-4}NR_GR_H$, $SO_2NR_GR_H$, and (CO)$NR_GR_H$; provided that where Ar is a pyridyl, each of $R_7$ and $R_8$ is H;

each of $R_C$, $R_D$, $R_E$, $R_F$, $R_G$, and $R_H$ is independently selected from H, $C_{1-4}$ alkyl, $C_{3-4}$ alkenyl, $C_{3-4}$ alkynyl, $C_{3-6}$ cycloalkyl, and phenyl; each of $NR_CR_D$, $NR_ER_F$, and $NR_GR_H$ can also be independently morpholinyl, piperazinyl, pyrrolidinyl, or piperadinyl;

each of $R_I$ and $R_J$ is independently H, methyl, or ethyl;

$R_K$ is $C_{1-4}$ alkyl, $C_{3-4}$ alkenyl, $C_{3-4}$ alkynyl, $C_{3-6}$ cycloalkyl, or phenyl;

X is O, S, or NH; and wherein each hydrocarbon radical or heterocyclic radical above is optionally substituted with between 1 and 3 substituents independently selected from halo, $C_{1-4}$ alkyl, $C_{3-6}$ cycloalkyl, $C_{2-4}$ alkenyl, $C_{2-4}$ alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 2 substituents independently selected from halo, $C_{1-2}$ alkyl, hydroxyl, amino, and $NO_2$;

or a pharmaceutically acceptable salt or $C_{1-7}$ ester thereof.

2. A compound of claim 1, having the following formula (I):

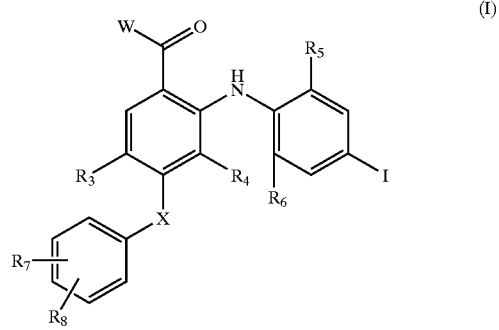

(I)

wherein

W is $OR_1$, $NR_2OR_1$, $NR_AR_B$, $NR_2NR_AR_B$, or $NR_2(CH_2)_{2-4}NR_AR_B$;

$R_1$ is H, $C_{1-8}$ alkyl, $C_{3-8}$ alkenyl, $C_{3-8}$ alkynyl, $C_{3-8}$ cycloalkyl, phenyl, (phenyl)$C_{1-4}$ alkyl, (phenyl)$C_{3-4}$ alkenyl, (phenyl)$C_{3-4}$ alkynyl, ($C_{3-8}$ cycloalkyl)-$C_{1-4}$ alkyl, ($C_{3-8}$ cycloalkyl)$C_{3-4}$ alkenyl, ($C_{3-8}$ cycloalkyl) $C_{3-4}$ alkynyl, $C_{3-8}$ heterocyclic radical, ($C_{3-8}$ heterocyclic radical)$C_{1-4}$ alkyl, ($C_{3-8}$ heterocyclic radical)$C_{3-4}$ alkenyl, ($C_{3-8}$ heterocyclic radical)$C_{3-4}$ alkynyl or $(CH_2)_{2-4}NR_AR_B$;

$R_2$ is H, phenyl, $C_{1-4}$ alkyl, $C_{3-4}$ alkenyl, $C_{3-8}$ alkynyl, $C_{3-8}$ cycloalkyl, or ($C_{3-8}$ cycloalkyl)-$C_{1-4}$ alkyl;

$R_A$ is H, $C_{1-6}$ alkyl, $C_{3-8}$ alkenyl, $C_{3-8}$ alkynyl, $C_{3-8}$ cycloalkyl, phenyl, ($C_{3-8}$ cycloalkyl)$C_{1-4}$ alkyl, ($C_{1-4}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical) $C_{1-4}$ alkyl, (aminosulfonyl)phenyl, [(aminosulfonyl) phenyl]$C_{1-4}$ alkyl, (aminosulfonyl)$C_{1-6}$ alkyl, (aminosulfonyl)$C_{3-6}$ cycloalkyl, or [(aminosulfonyl) $C_{3-6}$ cycloalkyl]$C_{1-4}$ alkyl;

$R_B$ is H, $C_{1-8}$ alkyl, $C_{3-8}$ alkenyl, $C_{3-8}$ alkynyl, $C_{3-8}$ cycloalkyl, or $C_{6-8}$ aryl;

$R_3$ is halo, $NO_2$, $SO_2NR_I(CH_2)_{2-4}NR_ER_F$, $SO_2NR_IR_K$ or (CO)T;

T is $C_{1-8}$ alkyl, $C_{3-8}$ cycloalkyl, $(NR_ER_F)C_{1-4}$ alkyl, $OR_F$, $NR_I(CH_2)_{2-4}NR_ER_F$, or $NR_ER_F$;

$R_4$ is H or F;

$R_5$ is H, methyl, halo, or $NO_2$;

$R_6$ is H, methyl, halo, or $NO_2$;

each of $R_7$ and $R_8$ is independently selected from H, halo, $C_{1-4}$ alkyl, $SO_2NR_I(CH_2)_{2-4}NR_GR_H$, $(CO)(CH_2)_{2-4}NR_GR_H$, $(CO)NR_I(CH_2)_{2-4}NR_GR_H$, $(CO)O(CH_2)_{2-4}NR_GR_H$, $SO_2NR_GR_H$, and (CO)$NR_GR_H$;

each of $R_C$, $R_D$, $R_E$, $R_F$, $R_G$, and $R_H$ is independently selected from H, $C_{1-4}$ alkyl, $C_{3-4}$ alkenyl, $C_{3-4}$ alkynyl, $C_{3-6}$ cycloalkyl, and phenyl; each of $NR_CR_D$, $NR_ER_F$, and $NR_GR_H$ can also be independently morpholinyl, piperazinyl, pyrrolidinyl, or piperadinyl;

each of $R_I$ and $R_J$ is independently H, methyl, or ethyl;

$R_K$ is $C_{1-4}$ alkyl, $C_{3-4}$ alkenyl, $C_{3-4}$ alkynyl, $C_{3-6}$ cycloalkyl, or phenyl;

X is O, S, or NH; and
wherein each hydrocarbon radical or heterocyclic radical above is optionally substituted with between 1 and 3 substituents independently selected from halo, $C_{1-4}$ alkyl, $C_{3-6}$ cycloalkyl, $C_{2-4}$ alkenyl, $C_{2-4}$ alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 2 substituents independently selected from halo, $C_{1-2}$ alkyl, hydroxyl, amino, and $NO_2$;
or a pharmaceutically acceptable salt or $C_{1-7}$ ester thereof.

3. A compound of claim 1, wherein $R_3$ is $NO_2$.

4. A compound of claim 1, wherein $R_4$ is fluoro.

5. A compound of claim 1, wherein each of $R_3$ and $R_4$ is independently fluoro.

6. A compound of claim 1, wherein $R_5$ is methyl, fluoro, or chloro.

7. A compound of claim 1, wherein $R_6$ is methyl, chloro, fluoro, nitro, or hydrogen.

8. A compound of claim 7, wherein $R_6$ is H.

9. A compound of claim 7, wherein $R_6$ is fluoro.

10. A compound of claim 1, wherein $R_K$ is methyl or ethyl.

11. A compound of claim 1, wherein $R_1$ is H, methyl, ethyl, propyl, isopropyl, isobutyl, benzyl, phenyl, phenethyl, allyl, $C_{2-5}$ alkenyl, $C_{3-6}$ cycloalkyl, $(C_{3-5}$ cycloalkyl$)C_{1-2}$ alkyl, $(C_{3-5}$ heterocyclic radical$)C_{1-2}$ alkyl, or $(CH_2)_{2-4}NR_CR_D$.

12. A compound of claim 11, wherein $R_1$ is H or $(C_{3-4}$ cycloalkyl$)$-$C_{1-2}$ alkyl.

13. A compound of claim 1, wherein $R_2$ is H or methyl.

14. A compound of claim 1, wherein $R_A$ is $C_{1-6}$ alkyl, $C_{3-8}$ alkenyl, $C_{3-8}$ alkynyl, $C_{3-8}$ cycloalkyl, or phenyl.

15. A compound of claim 1, wherein $R_A$ is H, methyl, ethyl, isobutyl, hydroxyethyl, phenyl, 2-piperidin-1-yl-ethyl, 2,3-dihydroxy-propyl, 3-[4-(2-hydroxyethyl)-piperazin-1-yl]-propyl, 2-pyrrolidin-1-yl-ethyl, or 2-diethylamino-ethyl; and $R_B$ is H; or where $R_B$ is methyl and $R_A$ is phenyl.

16. A compound of claim 1, wherein W is $NR_AR_B$ or $NR_2NR_AR_B$.

17. A compound of claim 1, wherein W is $NR_2(CH_2)_{2-4}NR_AR_B$ or $O(CH_2)_{2-3}NR_AR_B$.

18. A compound of claim 1, wherein W is $NR_2OR_1$.

19. A compound of claim 1, wherein W is $OR_B$.

20. A compound of claim 1, wherein $R_7$ is in the para position relative to X.

21. A compound of claim 20, wherein $R_7$ is iodo.

22. A compound of claim 1, wherein $R_8$ is in the ortho position relative to X.

23. A compound of claim 1 having the formula 2,4-bis-(2-chloro-4-iodo-phenylamino)-3-fluoro-5-nitro-benzoic acid.

24. A compound of claim 1 selected from: 2-(2-chloro-4-iodo-phenylamino)-3-fluoro-5-nitro4-(4-sulfamoyl-phenylamino)-benzoic acid; 2-(2-chloro-4-iodo-phenylamino)-3-fluoro-5-nitro-4-phenylamino-benzoic acid; 2-(2-chloro-4-iodo-phenylamino)-3-fluoro-5-nitro-4-phenoxy-benzoic acid; 2-(2-chloro-4-iodo-phenylamino)-3-fluoro-5-nitro-4-phenylsulfanyl-benzoic acid; 2-(2-chloro-4-iodo-phenylamino)-3-fluoro-4-(methyl-phenyl-amino)-5-nitro-benzoic acid; benzamide, 2-[(2-chloro-4-iodophenyl)amino]-3-fluoro-N-hydroxy-4-[[4-[[(2-hydroxyethyl)aminol-carbonyl]phenyl]amino]-5-nitro-; benzamide, 2-[(2-chloro-4-iodophenyl)amino]4-[[4-[(dimethylamino)carbonyl]phenyl]amino]-3-fluoro-N-hydroxy-5-nitro-; 2-(2-chloro-4-iodo-phenylamino)-3,5-difluoro-4-phenylamino-benzoic acid; 2-(2-chloro-4-iodo-phenylamino)-3-fluoro-5-nitro-4-(3-sulfamoyl-phenylamino)-benzoic acid; and 2-(2-chloro-4-iodo-phenylamino)-3-fluoro-5-nitro-4-(2-sulfamoyl-phenylamino)-benzoic acid; and the corresponding hydroxamic acids and cyclopropylmethyl hydroxamates.

25. A pharmaceutical composition comprising a compound of claim 1 and a pharmaceutically-acceptable carrier.

26. A method for treating a proliferative disease, said method comprising administering to a patient in need of such treatment a pharmaceutically-effective amount of a composition comprising a compound of claim 1.

27. A method of claim 26, wherein said proliferative disease is selected from psoriasis, restenosis, autoimmune disease, and atherosclerosis.

28. A method for treating cancer, said method comprising administering to a patient in need of such treatment a pharmaceutically-effective amount of a composition comprising a compound of claim 1.

29. A method of claim 28, wherein said cancer is MEK-related.

30. A method of claim 28, wherein said cancer is breast, lung, ovarian, pancreatic, renal, or colorectal cancer.

31. A method for treating, or ameliorating the sequelae of, a stroke, said method comprising administering to a patient in need of such treatment a pharmaceutically-effective amount of a composition comprising a compound of claim 1.

32. A method for treating, or ameliorating the sequelae of, heart failure, said method comprising administering to a patient in need of such treatment a pharmaceutically-effective amount of a composition comprising a compound of claim 1.

33. A method for treating or reducing the symptoms of xenograft rejection, said method comprising administering to an organ transplant, limb transplant, skin transplant, cell transplant, or bone marrow transplant patient a pharmaceutically-effective amount of a composition comprising a compound of claim 1.

34. A method for treating osteoarthritis, said method comprising administering to a patient in need of such treatment a pharmaceutically-effective amount of a composition comprising a compound of claim 1.

35. A method for treating rheumatoid arthritis, said method comprising administering to a patient in need of such treatment a pharmaceutically-effective amount of a composition comprising a compound of claim 1.

36. A method for treating asthma, said method comprising administering to a patient in need of such treatment a pharmaceutically-effective amount of a composition comprising a compound of claim 1.

37. A method for treating cystic fibrosis, said method comprising administering to a patient in need of such treatment a pharmaceutically-effective amount of a composition comprising a compound of claim 1.

38. A method for treating hepatomegaly, said method comprising administering to a patient in need of such treatment a pharmaceutically-effective amount of a composition comprising a compound of claim 1.

39. A method for treating cardiomegaly, said method comprising administering to a patient in need of such treatment a pharmaceutically-effective amount of a composition comprising a compound of claim 1.

40. A method for treating Alzheimer's disease, said method comprising administering to a patient in need of such treatment a pharmaceutically-effective amount of a composition comprising a compound of claim 1.

41. A method for treating a complication of diabetes, said method comprising administering to a patient in need of such treatment a pharmaceutically-effective amount of a composition comprising a compound of claim 1.

42. A method for treating septic shock, said method comprising administering to a patient in need of such treatment a pharmaceutically-effective amount of a composition comprising a compound of claim 1.

43. A method for treating cancer, said method comprising (a) administering to a patient in need of such treatment, a pharmaceutically-effective amount of a composition comprising a compound of claim 1, and (b) administering a therapy selected from radiation therapy and chemotherapy.

44. A method of claim 43, wherein said chemotherapy comprises a mitotic inhibitor.

45. A method of claim 39, wherein said mitotic inhibitor is selected from paclitaxel, docetaxel, vincristine, vinblastine, vinorelbine, and vinflunine.

46. A compound of claim 14, wherein $C_{1-6}$ alkyl, $C_{3-8}$ alkenyl, $C_{3-8}$ alkynyl, $C_{3-8}$ cycloalkyl, or phenyl is substituted by at least one hydroxyl group.

* * * * *